United States Patent [19]

Broadhurst et al.

[11] Patent Number: 5,205,852
[45] Date of Patent: Apr. 27, 1993

[54] ALKYLPHOSPHONAMIDATE HERBICIDES
[75] Inventors: Michael D. Broadhurst, Novato; Tsze H. Tsang, El Cerrito, both of Calif.
[73] Assignee: Imperial Chemical Industries PLC, London, United Kingdom
[21] Appl. No.: 792,532
[22] Filed: Nov. 12, 1991
[51] Int. Cl.$^5$ ............... A01N 57/04; A01N 57/06; C07F 9/44
[52] U.S. Cl. ................. 504/199; 558/195; 558/199; 558/200; 504/195; 504/196
[58] Field of Search ............ 546/21; 558/195, 199, 558/200; 71/86, 87

[56] References Cited

U.S. PATENT DOCUMENTS

| | | | |
|---|---|---|---|
| 2,714,064 | 7/1955 | Morris et al. | 71/71 |
| 2,765,276 | 10/1956 | Van Winkle et al. | 252/32.5 |
| 3,010,986 | 11/1961 | Reetz | 558/98 |
| 3,253,062 | 5/1966 | Reetz | 558/199 |
| 3,260,712 | 7/1966 | Schrader | 558/200 X |
| 3,487,151 | 12/1969 | Tilles et al. | 514/83 |
| 3,576,922 | 4/1971 | Gaughan | 558/201 |
| 3,636,206 | 1/1972 | Gaughan | 514/135 |
| 3,666,842 | 5/1972 | Aichenegg et al. | 558/199 |
| 3,726,948 | 4/1973 | Botts | 558/166 |
| 3,880,960 | 4/1975 | Sirrenberg et al. | 558/200 X |
| 3,928,018 | 12/1975 | Randall | 71/86 |
| 4,046,885 | 9/1977 | Walsh | 514/113 |
| 4,129,660 | 12/1978 | Warolin et al. | 514/99 |
| 4,419,440 | 12/1983 | Kuhnert et al. | 430/377 |

FOREIGN PATENT DOCUMENTS

| | | |
|---|---|---|
| 963876 | 6/1957 | Fed. Rep. of Germany . |
| 3316891 | 8/1984 | Fed. Rep. of Germany . |
| 145575 | 6/1962 | U.S.S.R. . |
| 170245 | 4/1965 | U.S.S.R. . |
| 896956 | 5/1962 | United Kingdom . |
| 1350286 | 1/1974 | United Kingdom . |

OTHER PUBLICATIONS

Chem. Abstr. 1987, 106(11), 84726j.
Chem. Abstr. 1975, 82(5), 30567a.
Chem. Abstr. 1965, 62, 13176f.
Almasi et al., J. Prakt., Chem 321, 913 (1979).
Bakumenko et al., Khim. Sel'sk Khoz. 4, 691 (1966).
Cadogan, J. Chem. Soc. Part I, 1079 (1957).
Genkina, et al., Zh. Obshch. Khim. 40, 1496 (1970).
Grapov, et al., Zh. Obshch. Khim. 38, 1751 (1968).
Grapov, et al., Khim. Primen. Fosforg. Soedin., Tr. Konf. 379 (1972).
Kamai, et al., Zh. Obshch. Khim. 42, 1295 (1972).
Keay, J. Org. Chem. 28, 329 (1963).
Kruglov, et al., Ber. Synth. Wachstumsregl., 12th, 205 (1979).
Mel'nikov, et al., CA 71, 80074f (1969).
Pudovik, et al., Zh. Obshch. Khim 39, 1890 (1969).
Razumov, et al., C.A. 52, 237g (1958).
Shokol, et al., Zh. Obshch. Khim. 36, 1636 (1966).
Tomchina, et al., Zh. Obshch. Khim, 38, 564 (1968).

Primary Examiner—Mary C. Lee
Assistant Examiner—Michael G. Ambrose
Attorney, Agent, or Firm—Joel G. Ackerman

[57] ABSTRACT

Herbicidal compounds have the formula

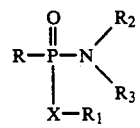

in which
R is $C_3$-$C_6$ alkyl or $C_3$-$C_6$ cycloalkyl;
X is oxygen or sulfur;
$R_1$ is $C_1$-$C_{12}$ alkyl, $C_3$-$C_6$ cycloalkyl optionally substituted with up to two $C_1$-$C_3$ alkyl groups, phenyl, or substituted phenyl having from 1 to 2 substituents selected from halo, nitro, $C_1$-$C_4$ alkyl, $C_1$-$C_4$ alkoxy, $C_1$-$C_4$ thioalkyl, $C_3$-$C_4$ alkenyl, $C_1$-$C_4$ alkoxycarbonyl, and phenyl;
$R_2$ is hydrogen, $C_1$-$C_6$ alkyl or $C_3$-$C_6$ cycloalkyl; and
$R_3$ is $C_2$-$C_6$ alkyl, $C_3$-$C_6$ cycloalkyl, phenyl or substituted phenyl having from 1 to 2 substituents selected from $C_1$-$C_4$ alkyl, $C_1$-$C_4$ alkoxy, $C_1$-$C_4$ haloalkyl and halogen;
provided that if $R_2$ is hydrogen, $R_3$ is not phenyl or substituted phenyl;
or $R_2$ and $R_3$ taken together with the nitrogen atom form a 4–8 membered ring, optionally including an oxygen heteroatom.

14 Claims, No Drawings

ALKYLPHOSPHONAMIDATE HERBICIDES

FIELD OF THE INVENTION

This invention relates to certain alkylphosphonamidate compounds which demonstrate herbicidal activity.

A number of methyl and halomethyl aryl ester phosphonamidates were found to be herbicidal by Soviet researchers in the 1960's and 1970's. These are disclosed in a number of references including Bakumenko et al, Khim. Sel' sk Khoz., vol. 4, p. 691 (1966); Grapov et al, Zh. Obshch. Khim., vol. 38, p. 1751 (1968); id. Khim. Primen. Fosforg. Soedin., Tr. Konf. 379 (1972); Mel'nikov et al, Russian patents 170,245 (1965) and 216,380 (1969) and Zh. Obshch. Khim., vol. 38, p. 2648 (1968); and Kruglov et al, Ber. Synth. Wachstumsregl., 12th, 205 (1979). The most important compounds of this type appear to have been the P-chloromethyl, Isophos series:

CH$_2$ClP(O)(NH-sec.-butyl)(O-2,4-dichlorophenyl) (Isophos 1);
CH$_2$ClP(O)(NH-n-propyl)(O-2,4-dichlorophenyl) (Isophos 2); and
CH$_2$ClP(O)(NH-sec.-butyl)(O-2-chloro-p-tolyl) (Isophos 3).

In the same time period, Kamai et al, Zh. Obshch. Khim., vol. 42, p. 1295 (1972) reported synthesizing a number of organophosphorus compounds, including two ethylphosphonamidates, and characterized them all as showing "weak herbicidal activity."

Some herbicidal alkyl phosphonodiamidates are disclosed in British Patent 1,350,286 of Nissan Chemical Industries, Ltd., and also in Bakumenko et al, supra.

DESCRIPTION OF THE INVENTION

It has now been found that a number of propyl and higher alkyl phosphonamidate esters, as well as cycloalkyl phosphonamidates, exhibit herbicidal activity, particularly as post-emergent herbicides.

In one aspect, therefore, this invention comprises controlling undesirable vegetation (particularly by post-emergent application, i.e. after the vegetation has emerged) by application to the vegetation or the locus thereof of an herbicidally effective amount of a compound having the formula

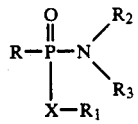

in which:
R is C$_3$-C$_6$ alkyl or C$_3$-C$_6$ cycloalkyl;
X is oxygen or sulfur;
R$_1$ is C$_2$-C$_{12}$ alkyl, C$_3$-C$_6$ cycloalkyl optionally substituted with up to 2 C$_1$-C$_3$ alkyl groups, phenyl, or substituted phenyl having from 1 to 2 substituents selected from halo, nitro, C$_1$-C$_4$ alkyl, C$_1$-C$_4$ alkoxy, C$_1$-C$_4$ thioalkyl, C$_3$-C$_4$ alkenyl, C$_1$-C$_4$ alkoxycarbonyl, and phenyl;
R$_2$ is hydrogen, C$_1$-C$_6$ alkyl or C$_3$-C$_6$ cycloalkyl; and
R$_3$ is C$_2$-C$_6$ alkyl, C$_3$-C$_6$ cycloalkyl, phenyl or substituted phenyl having from 1 to 2 substitutents selected from C$_1$-C$_4$ alkyl, C$_1$-C$_4$ alkoxy, C$_1$-C$_4$ haloalkyl and halogen;
provided that if R$_2$ is hydrogen, R$_3$ is not phenyl or substituted phenyl;
or R$_2$ and R$_3$ taken together with the nitrogen atom form a 4-8 membered ring, optionally including an oxygen heteroatom.

Some compounds of this general type are disclosed, either specifically or generically, in the prior art, for instance in U.S. Pat. No. 3,636,206 of Gaughan (generically, as insecticides) and in Razumov, CA vol. 52, p. 237g (1958) as cholinesterase inhibitors.

Most of the compounds of the type mentioned above are, however, novel and form another aspect of this invention, namely herbicidal compounds having the formula

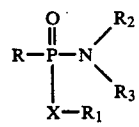

in which:
R is C$_3$-C$_6$ alkyl or C$_3$-C$_6$ cycloalkyl;
X is oxygen or sulfur;
R$_1$ is C$_2$-C$_{12}$ alkyl, C$_3$-C$_6$ cycloalkyl optionally substituted with up to 2 C$_1$-C$_3$ alkyl groups, phenyl, or substituted phenyl having from 1 to 2 substituents selected from halo, nitro, C$_1$-C$_4$ alkyl, C$_1$-C$_4$ alkoxy, Cl-C$_4$ thioalkyl, C$_3$-C$_4$ alkenyl, C$_1$-C$_4$ alkoxycarbonyl, and phenyl;
R$_2$ is hydrogen, C$_1$-C$_6$ alkyl or C$_3$-C$_6$ cycloalkyl; and
R$_3$ is C$_2$-C$_6$ alkyl, C$_3$-C$_6$ cycloalkyl, phenyl or substituted phenyl having from 1 to 2 substituents selected from C$_1$-C$_4$ alkyl, C$_1$-C$_4$ alkoxy, Cl-C$_4$ haloalkyl and halogen;
provided that if R$_2$ is hydrogen, R$_3$ is not phenyl or substituted phenyl;
or R$_2$ and R$_3$ taken together with the nitrogen atom form a 4-8 membered ring, optionally including an oxygen heteroatom;
provided that:
(1) if X is sulfur, R$_2$ is not hydrogen; and
(2) if R is isopropyl and X is oxygen, then none of R$_1$, R$_2$ or R$_3$ are ethyl.

Preferred compounds are those in which R is C$_3$-C$_6$ alkyl or C$_5$-C$_6$ cycloalkyl; X is oxygen or sulfur; R$_1$ is C$_2$-C$_8$ alkyl, or C$_3$-C$_6$ cycloalkyl optionally substituted with one methyl group; and (a) R$_2$ is C$_3$-C$_6$ alkyl and R$_3$ is C$_3$-C$_6$ alkyl or C$_5$-C$_6$ cycloalkyl; (b) R$_2$ is hydrogen and R$_3$ is C$_3$-C$_6$ alkyl or C$_5$-C$_6$ cycloalkyl or (c) R$_2$ is C$_1$-C$_4$ alkyl and R$_3$ is phenyl or substituted phenyl.

The term "alkyl" includes straight and branched chained saturated acyclic hydrocarbyl moieties having the indicated number of carbon atoms. Preferred alkyl groups include ethyl, n-propyl, isopropyl, n-butyl, s-butyl, t-butyl, i-butyl, n-amyl, n-hexyl and n-octyl. The term "cycloalkyl" includes saturated cyclical hydrocarbyl moieties, such as cyclopentyl and cyclohexyl. The terms "halogen" or "halo" include chloro, bromo, fluoro and iodo. Substituted phenyl groups may contain one or two of the indicated substituents, which may be the same or different. Preferred substituents are chloro, fluoro, nitro, methyl, ethyl, i-propyl, t-butyl, methoxy, ethoxy, trifluoromethyl, and combinations of two of these, which may be the same or different.

Rings containing R$_2$ and R$_3$, with a nitrogen atom are, for instance, pyrrolidinyl, piperidinyl, morpholinyl, and the like.

As used herein, the term "herbicide" means a compound or composition which adversely controls or modifies the growth of plants. By the term "herbicidally effective amount" is meant any amount of such compound or composition which causes an adverse modifying effect upon the growth of plants. By "plants", it is meant germinant seeds, emerging seedlings and established vegetation, including roots and above-ground portions. Such controlling or modifying effects include all deviations from natural development, such as killing, retardation, defoliation, desiccation, regulation, stunting, tillering, leaf burn, dwarfing, and the like.

The compounds of this invention have been found to be active herbicides, particularly post-emergent herbicides; i.e. they may be applied to control or kill existing vegetation which has already emerged from the soil. Some of the compounds of this invention have demonstrated such post-emergence herbicidal activity in a relatively short time, and against some weeds, with a very strong effect. Herbicides having such rapid and extensive post-emergence activity are sometimes referred to as "contact and burn" or "burn-down" herbicides and are used, among other applications, for clearing vegetation from land such as building lots, highway median strips, railroad track beds, and crop land prior to planting or in minimum till or no-till farming. Some of the compounds of this invention also demonstrate pre-emergence activity, that is, control or killing of vegetation by application prior to the emergence of vegetation from the soil. Pre-emergence herbicides may be applied by techniques such as incorporation into, or spraying or spreading onto, the surface of the soil.

Compounds showing "contact-and-burn" effect, but little or no pre-emergence activity, may be useful in clearing land prior to planting since planting of a crop can be done relatively soon after the herbicide is applied.

The compounds of this invention may be prepared from starting phosphonodichlorides, amines and appropriate alcohols or thiols or their metal (particularly alkali metal) salts, in one or two steps, by the general reaction

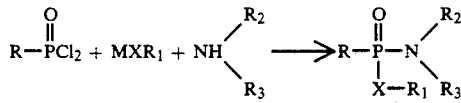

in which M is hydrogen or an alkali metal (preferably sodium or potassium).

This process may be conducted in a single step, or stepwise, in sequence. In the latter case, the phosphonyl dichloride is reacted first with one equivalent of an amine, together with triethylamine, followed by isolation and purification of the chloroamide intermediate, which can then be treated with an alkali metal salt of the appropriate alcohol. Alternatively, the phosphonyl dichloride may be treated with an alcohol in the presence of a tertiary amine base such as triethylamine, and the intermediate chloroester reacted with two equivalents of the appropriate amine, preferably without isolation.

Single-step process of this type in general are carried out at temperatures of from about $-60°$ to about $+50°$ C., preferably from about $-20°$ to about $+25°$ C. Those in which the first step is a reaction between the dichloride and an alcohol conduct this step at a temperature of between about $-40°$ and $+25°$ C., with the second step at 25° C. up to reflux temperature.

All processes are carried out in the presence of a solvent, such as an aromatic solvent (preferably toluene) or tetrahydrofuran.

The following is an example of the preparation of a compound of this invention.

EXAMPLE

Preparation of N,N-di-(n-propyl)-O-isopropyl s-butyl-phosohonamidate (Compound No. 21 herein)

A. Preparation of N,N-di-(n-propyl) s-butylphosphonochloridae. To a flask containing a solution of 12 g (68.6 mmol) s-butylphosphonodichloride in 100 mL of toluene (under cooling), there was added dropwise 24 mL (172 mmol) triethylamine. The mixture was stirred for 30 minutes, cooled to $-78°$ C., and 11.2 mL (82 mmol) di-(n-propyl)amine added dropwise. The mixture was stirred for 4 days and quenched with 100 mL of 5% HCl. The organic phase was separated, washed, dried, filtered, and concentrated to give a light brown oil. The crude product was distilled, giving 9.4 g of a colorless oil, shown by gas chromatography to be 100% pure.

B. To a flask containing a solution of 1.25 mL (13.5 mmol) 2-propanethiol in 30 mL toluene, was added 8.5 mL (12.8 mmol) of a 1.5 M solution of lithium diisopropylamine in cyclohexane, with cooling. The mixture was stirred for 30 minutes and cooled to $-78°$ C. Then, 3.0 g (12.5 mmol) N,N-di(n-propyl) sec.-butyl phosphonochloridate was added dropwise. The mixture was again stirred for 30 minutes, then quenched with 50 mL water. The organic phase was separated, dried, filtered and concentrated, giving a light brown oil. The crude product was purified by flash chromatography over silica gel, eluting with 25% ethyl acetate-hexane to give 2.2 g of a colorless oil, shown by gas chromatography to be 96% pure. The structure was confirmed as the desired product by spectroscopic analyses.

Table I depicts representative compounds of this invention, prepared by one of the processes described above. Most or all compounds were obtained as oils. Structures were confirmed by spectroscopic analyses.

TABLE I

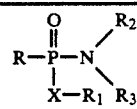

| Compound No. | R | X | $R_1$ | $R_2$ | $R_3$ |
|---|---|---|---|---|---|
| 1. | $n\text{-}C_4H_9$ | S | $sec\text{-}C_4H_9$ | $n\text{-}C_3H_7$ | $n\text{-}C_3H_7$ |
| 2. | $n\text{-}C_6H_{13}$ | S | $sec\text{-}C_4H_9$ | $n\text{-}C_3H_7$ | $n\text{-}C_3H_7$ |
| 3. | $n\text{-}C_4H_9$ | O | $sec\text{-}C_4H_9$ | $n\text{-}C_3H_7$ | $n\text{-}C_3H_7$ |
| 4. | $n\text{-}C_6H_{13}$ | O | $sec\text{-}C_4H_9$ | $n\text{-}C_3H_7$ | $n\text{-}C_3H_7$ |
| 5. | $n\text{-}C_4H_9$ | O | $i\text{-}C_3H_7$ | $n\text{-}C_3H_7$ | $n\text{-}C_3H_7$ |
| 6. | $n\text{-}C_6H_{13}$ | S | $n\text{-}C_3H_7$ | $C_2H_5$ | $C_2H_5$ |
| 7. | $i\text{-}C_3H_7$ | O | $2,6\text{-}Cl,4\text{-}NO_2C_6H_2$ | $n\text{-}C_3H_7$ | $n\text{-}C_3H_7$ |
| 8. | $sec\text{-}C_4H_9$ | O | $sec\text{-}C_4H_9$ | $n\text{-}C_3H_7$ | $n\text{-}C_3H_7$ |

TABLE I-continued $$R-\underset{\underset{X-R_1}{|}}{\overset{\overset{O}{\|}}{P}}-N\underset{R_3}{\overset{R_2}{<}}$$

| Compound No. | R | X | R₁ | R₂ | R₃ |
|---|---|---|---|---|---|
| 9. | cyclopentyl | O | sec-C₄H₉ | n-C₃H₇ | n-C₃H₇ |
| 10. | sec-C₄H₉ | O | sec-C₄H₉ | H | tetrahydrothiopyranyl |
| 11. | sec-C₄H₉ | O | sec-C₄H₉ | C₂H₅ | C₂H₅ |
| 12. | sec-C₄H₉ | O | sec-C₄H₉ | H | i-C₄H₉ |
| 13. | n-C₆H₁₃ | S | sec-C₄H₉ | C₂H₅ | C₂H₅ |
| 14. | n-C₆H₁₃ | O | C₆H₅ | C₂H₅ | C₂H₅ |
| 15. | cyclopentyl | O | sec-C₄H₉ | H | tetrahydrothiopyranyl |
| 16. | cyclopentyl | O | sec-C₄H₉ | H | n-C₆H₁₃ |
| 17. | tetrahydrothiopyranyl | O | sec-C₄H₉ | H | tetrahydrothiopyranyl |
| 18. | tetrahydrothiopyranyl | O | sec-C₄H₉ | H | n-C₆H₁₃ |
| 19. | tetrahydrothiopyranyl | O | sec-C₄H₉ | H | i-C₄H₉ |
| 20. | sec-C₄H₉ | S | n-C₃H₇ | n-C₃H₇ | n-C₃H₇ |
| 21. | sec-C₄H₉ | S | i-C₃H₇ | n-C₃H₇ | n-C₃H₇ |
| 22. | sec-C₄H₉ | S | C₆H₅ | n-C₃H₇ | n-C₃H₇ |
| 23. | n-C₃H₇ | S | n-C₃H₇ | n-C₃H₇ | n-C₃H₇ |
| 24. | n-C₃H₇ | O | sec-C₄H₉ | H | i-C₄H₉ |
| 25. | n-C₃H₇ | O | sec-C₄H₉ | H | n-C₆H₁₃ |
| 26. | n-C₃H₇ | O | sec-C₄H₉ | H | n-C₃H₇ |
| 27. | n-C₃H₇ | O | sec-C₄H₉ | H | tetrahydrothiopyranyl |
| 28. | n-C₃H₇ | O | sec-C₄H₉ | n-C₃H₇ | n-C₃H₇ |
| 29. | n-C₃H₇ | S | C₆H₅ | n-C₃H₇ | n-C₃H₇ |
| 30. | n-C₃H₇ | O | sec-C₄H₉ | C₂H₅ | C₂H₅ |
| 31. | n-C₃H₇ | O | n-C₃H₇ | n-C₃H₇ | n-C₃H₇ |
| 32. | n-C₃H₇ | O | C₂H₅ | n-C₃H₇ | n-C₃H₇ |
| 33. | n-C₃H₇ | O | i-C₃H₇ | n-C₃H₇ | n-C₃H₇ |
| 34. | n-C₃H₇ | O | n-C₈H₁₇ | n-C₃H₇ | n-C₃H₇ |
| 35. | sec-C₄H₉ | O | n-C₈H₁₇ | n-C₃H₇ | n-C₃H₇ |
| 36. | n-C₃H₇ | O | 4-ClC₆H₄ | n-C₃H₇ | n-C₃H₇ |
| 37. | n-C₃H₇ | O | 2,4-ClC₆H₃ | n-C₃H₇ | n-C₃H₇ |
| 38. | n-C₃H₇ | O | 4-CH₃C₆H₄ | n-C₃H₇ | n-C₃H₇ |
| 39. | n-C₃H₇ | O | 2-ClC₆H₄ | n-C₃H₇ | n-C₃H₇ |
| 40. | n-C₃H₇ | O | 4-NO₂C₆H₄ | n-C₃H₇ | n-C₃H₇ |

TABLE I-continued $$R-\underset{\underset{X-R_1}{\|}}{\overset{\overset{O}{\|}}{P}}-N\overset{R_2}{\underset{R_3}{}}$$

| Compound No. | R | X | R₁ | R₂ | R₃ |
|---|---|---|---|---|---|
| 41. | n-C₃H₇ | O | 3-ClC₆H₄ | n-C₃H₇ | n-C₃H₇ |
| 42. | n-C₃H₇ | S | i-C₃H₇ | n-C₄H₉ | n-C₄H₉ |
| 43. | n-C₃H₇ | S | sec-C₄H₉ | n-C₄H₉ | n-C₄H₉ |
| 44. | sec-C₄H₉ | O | i-C₃H₇ | n-C₄H₉ | n-C₄H₉ |
| 45. | sec-C₄H₉ | O | sec-C₄H₉ | n-C₄H₉ | n-C₄H₉ |
| 46. | sec-C₄H₉ | S | i-C₃H₇ | n-C₄H₉ | n-C₄H₉ |
| 47. | sec-C₄H₉ | S | sec-C₄H₉ | n-C₄H₉ | n-C₄H₉ |
| 48. | n-C₄H₉ | O | C₂H₅ | n-C₃H₇ | n-C₃H₇ |
| 49. | n-C₄H₉ | O | n-C₃H₇ | n-C₃H₇ | n-C₃H₇ |
| 50. | n-C₄H₉ | O | n-C₄H₉ | n-C₃H₇ | n-C₃H₇ |
| 51. | n-C₃H₇ | O | cyclopentyl | n-C₃H₇ | n-C₃H₇ |
| 52. | n-C₄H₉ | O | tetrahydrothiopyranyl | n-C₃H₇ | n-C₃H₇ |
| 53. | n-C₃H₇ | O | i-C₃H₇ | n-C₃H₇ | n-C₃H₇ |
| 54. | n-C₃H₇ | O | sec-C₄H₉ | n-C₄H₉ | n-C₄H₉ |
| 55. | cyclopentyl | S | sec-C₄H₉ | n-C₃H₇ | n-C₃H₇ |
| 56. | n-C₄H₉ | O | n-C₈H₁₇ | n-C₃H₇ | n-C₃H₇ |
| 57. | n-C₄H₉ | S | C₆H₅ | n-C₃H₇ | n-C₃H₇ |
| 58. | n-C₄H₉ | O | n-C₆H₁₃ | n-C₃H₇ | n-C₃H₇ |
| 59. | n-C₄H₉ | O | sec-C₄H₉ | n-C₄H₉ | n-C₄H₉ |
| 60. | n-C₄H₉ | O | sec-C₄H₉ | H | n-C₄H₉ |
| 61. | n-C₄H₉ | S | sec-C₄H₉ | n-C₄H₉ | n-C₄H₉ |
| 62. | tetrahydrothiopyranyl | S | sec-C₄H₉ | n-C₃H₇ | n-C₃H₇ |
| 63. | n-C₄H₉ | O | sec-C₄H₉ | H | tetrahydrothiopyranyl |
| 64. | cyclopentyl | S | i-C₃H₇ | n-C₃H₇ | n-C₃H₇ |
| 65. | cyclopentyl | S | n-C₃H₇ | n-C₃H₇ | n-C₃H₇ |
| 66. | tetrahydrothiopyranyl | O | sec-C₄H₉ | n-C₃H₇ | n-C₃H₇ |
| 67. | tetrahydrothiopyranyl | S | n-C₃H₇ | n-C₃H₇ | n-C₃H₇ |

TABLE I-continued

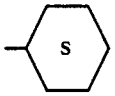

| Compound No. | R | X | R₁ | R₂ | R₃ |
|---|---|---|---|---|---|
| 68. | $n\text{-}C_4H_9$ | O | $C_2H_5$ | H | (2-thienyl) |
| 69. | $n\text{-}C_4H_9$ | O | $sec\text{-}C_4H_9$ | H | $n\text{-}C_6H_{13}$ |
| 70. | $n\text{-}C_4H_9$ | O | $C_6H_5$ | $n\text{-}C_3H_7$ | $n\text{-}C_3H_7$ |
| 71. | $n\text{-}C_4H_9$ | S | $sec\text{-}C_4H_9$ | $C_2H_5$ | $C_2H_5$ |
| 72. | $n\text{-}C_4H_9$ | S | $i\text{-}C_3H_7$ | $n\text{-}C_3H_7$ | $n\text{-}C_3H_7$ |
| 73. | $n\text{-}C_4H_9$ | S | $n\text{-}C_3H_7$ | $n\text{-}C_3H_7$ | $n\text{-}C_3H_7$ |
| 74. | $n\text{-}C_4H_9$ | S | $n\text{-}C_4H_9$ | $n\text{-}C_3H_7$ | $n\text{-}C_3H_7$ |
| 75. | $n\text{-}C_4H_9$ | O | $n\text{-}C_{12}H_{25}$ | $n\text{-}C_3H_7$ | $n\text{-}C_3H_7$ |
| 76. | $n\text{-}C_4H_5$ | O | $sec\text{-}C_4H_9$ | $C_2H_5$ | $C_2H_5$ |
| 77. | $n\text{-}C_4H_9$ | O | $2\text{-}CH_3C_6H_4$ | $n\text{-}C_3H_7$ | $n\text{-}C_3H_7$ |
| 78. | $n\text{-}C_3H_7$ | O | $C_6H_5$ | $n\text{-}C_3H_7$ | $n\text{-}C_3H_7$ |
| 79. | $n\text{-}C_4H_9$ | O | $n\text{-}C_5H_{11}$ | $n\text{-}C_3H_7$ | $n\text{-}C_3H_7$ |
| 80. | $n\text{-}C_4H_9$ | O | $-CH(CH_3)C_3H_7$ | $n\text{-}C_3H_7$ | $n\text{-}C_3H_7$ |
| 81. | $n\text{-}C_4H_9$ | O | $-CH(C_2H_5)_2$ | $n\text{-}C_3H_7$ | $n\text{-}C_3H_7$ |
| 82. | $n\text{-}C_3H_7$ | O | $n\text{-}C_6H_{13}$ | $n\text{-}C_4H_9$ | $n\text{-}C_4H_9$ |
| 83. | $n\text{-}C_3H_7$ | O | $2\text{-}(t\text{-}C_4H_9)C_6H_4$ | $n\text{-}C_3H_7$ | $n\text{-}C_3H_7$ |
| 84. | $n\text{-}C_4H_9$ | O | $sec\text{-}C_4H_9$ | $CH_3$ | $C_6H_5$ |
| 85. | $n\text{-}C_3H_7$ | O | $sec\text{-}C_4H_9$ | $CH_3$ | $C_6H_5$ |
| 86. | $n\text{-}C_3H_7$ | O | $2\text{-}t\text{-}C_4H_9-C_6H_4$ | $C_2H_5$ | $C_2H_5$ |
| 87. | $n\text{-}C_3H_7$ | O | $2\text{-}OCH_3-C_6H_4$ | $n\text{-}C_3H_7$ | $n\text{-}C_3H_7$ |
| 88. | $n\text{-}C_3H_7$ | O | $2\text{-}OC_2H_5-C_6H_4$ | $n\text{-}C_3H_7$ | $n\text{-}C_3H_7$ |
| 89. | $n\text{-}C_3H_7$ | O | $2\text{-}SCH_3-C_6H_4$ | $n\text{-}C_3H_7$ | $n\text{-}C_3H_7$ |
| 90. | $n\text{-}C_3H_7$ | O | $2\text{-}CH_3-C_6H_4$ | $n\text{-}C_3H_7$ | $n\text{-}C_3H_7$ |
| 91. | $n\text{-}C_3H_7$ | O | $2\text{-}C_2H_5-C_6H_4$ | $n\text{-}C_3H_7$ | $n\text{-}C_3H_7$ |
| 92. | $n\text{-}C_3H_7$ | O | $2\text{-}(CH_2CH=CH_2)C_6H_4$ | $n\text{-}C_3H_7$ | $n\text{-}C_3H_7$ |
| 93. | $n\text{-}C_3H_7$ | O | $2\text{-}(i\text{-}C_3H_7)-C_6H_4$ | $n\text{-}C_3H_7$ | $n\text{-}C_3H_7$ |
| 94. | $n\text{-}C_3H_7$ | O | $2\text{-}C_6H_5-C_6H_4$ | $n\text{-}C_3H_7$ | $n\text{-}C_3H_7$ |
| 95. | $n\text{-}C_3H_7$ | O | $2\text{-}(C_2H_5OCO)-C_6H_4$ | $n\text{-}C_3H_7$ | $n\text{-}C_3H_7$ |
| 96. | $n\text{-}C_3H_7$ | O | $3\text{-}(t\text{-}C_4H_9)-C_6H_4$ | $n\text{-}C_3H_7$ | $n\text{-}C_3H_7$ |
| 97. | $n\text{-}C_3H_7$ | O | $4\text{-}(t\text{-}C_4H_9)-C_6H_4$ | $n\text{-}C_3H_7$ | $n\text{-}C_3H_7$ |
| 98. | $n\text{-}C_3H_7$ | O | $2\text{-}(sec\text{-}C_4H_9)-C_6H_4$ | $n\text{-}C_3H_7$ | $n\text{-}C_3H_7$ |
| 99. | $i\text{-}C_4H_9$ | O | $sec\text{-}C_4H_9$ | $n\text{-}C_3H_7$ | $n\text{-}C_3H_7$ |

Herbicidal Activity Tests

Compounds of Table I were tested for herbicidal activity as follows:

The herbicidal effect was observed by comparing the extent of weed control in test flats treated with the compounds against that occurring in similar non-treated control flats. All were applied at 3.57 lb/A (4 kg/ha) to pre-emergence and post-emergence screening flats. An 80 gal/A (748.3 1/ha) spray volume was utilized. Post-emergence flats were seeded 12 days prior to treatment. Pre-emergence flats were seeded one day prior to treatment. Overhead watering of pre-emergence flats and soil surface watering of post-emergence flats, so as to avoid wetting the foliage, were carried out for the duration of the test.

Weed seeds were planted in a flat at a seed depth of 0.5 inch (1 3 cm). Soil for flats was prepared using loam soil fortified with 17—17—17 fertilizer (N—P₂O₅—K₂O on a weight basis) and Captan 80W fungicide. The test weeds were as follows:

| COMMON NAME | SCIENTIFIC NAME |
|---|---|
| green foxtail | *Setaria viridis* |
| watergrass | *Echinochloa crusgalli* |
| wild oat | *Avena fatua* |
| annual morning glory | *Ipomoea purpurea* |
| velvetleaf | *Abutilon theophrasti* |
| wild mustard | *Brassica kaber* |
| yellow nutsedge | *Cyperus esculentus* |

The spray solutions were prepared by dissolving 240 mg of test compound in 20 ml of acetone containing 1% polyoxyethylene sorbitan monolaurate emulsifier, then adding 20 ml of water to the resulting solution. The stock solutions were applied using a linear spray table. Pre-emergence flats are raised to the level of the post-emergence foliage canopy by setting the flats on a wooden block.

The degree of weed control was visually assessed and recorded as percentage control compared to the growth of the same species in an untreated check flat of the same age. The rating scale ranges from 0 to 100%, where 0 equals no effect with plant growth equal to the untreated control, and 100 equals complete kill.

Ratings were taken in pre-emergence tests approximately 18 days after treatment (DAT). In post-emergence tests, ratings were taken at two intervals. On the sixth day after treatment, overall control was rated, as an indication of total vegetative control, or "contact and burn" activity. Approximately 18 days after treatment, the tests were rated for overall post-emergence activity.

Results are listed in Table II below, expressed as average control of the three grassy (GR) (wild oat, watergrass, foxtail) and three broadleaf weeds (BL) (morning glory, mustard, velvetleaf), and of nutsedge (NS).

TABLE II

| | % Control, 4 kg/ha | | | | | | | | |
|---|---|---|---|---|---|---|---|---|---|
| | Pre-emergence | | | Post-emergence | | | | | |
| | 18 DAT | | | 6 DAT | | | 18 DAT | | |
| Compound No. | GR avg. | Bl avg. | NS | GR avg. | BL avg. | NS | GR avg. | BL avg. | NS |
| 1. | 30 | 33 | 0 | 90 | 100 | 20 | 97 | 100 | 10 |
| 2. | 33 | 33 | 0 | 90 | 90 | 10 | 97 | 100 | 10 |
| 3. | 0 | 0 | 0 | 90 | 100 | 10 | 83 | 100 | 0 |
| 4. | 0 | 0 | 0 | 85 | 90 | 5 | 83 | 83 | 0 |
| 5. | 17 | 67 | 0 | 90 | 90 | 5 | 97 | 100 | 5 |
| 6. | 0 | 0 | 0 | 30 | 100 | 0 | 20 | 100 | 0 |
| 7. | 0 | 0 | 0 | 0 | 30 | 0 | 0 | 33 | 0 |
| 8. | 33 | 0 | 0 | 60 | 80 | 10 | 53 | 87 | 10 |
| 9. | 50 | 50 | 0 | 60 | 100 | 10 | 73 | 100 | 10 |
| 10. | 17 | 33 | 0 | 20 | 80 | 0 | 10 | 100 | 0 |
| 11. | 0 | 0 | 0 | 20 | 80 | 0 | 13 | 67 | 0 |
| 12. | 20 | 73 | 0 | 10 | 20 | 0 | 10 | 3 | 0 |
| 13. | 0 | 33 | 0 | 40 | 50 | 10 | 23 | 43 | 0 |
| 14. | 0 | 0 | 0 | 20 | 50 | 10 | 17 | 62 | 0 |
| 15. | 33 | 57 | 0 | 70 | 90 | 0 | 10 | 65 | 5 |
| 16. | 0 | 0 | 0 | 80 | 90 | 0 | 15 | 68 | 0 |
| 17. | 37 | 75 | 0 | 40 | 80 | 0 | 33 | 97 | 0 |
| 18. | 0 | 0 | 0 | 80 | 100 | 0 | 8 | 100 | 0 |
| 19. | 55 | 77 | 0 | 30 | 90 | 0 | 35 | 98 | 10 |
| 20. | 0 | 52 | 0 | 90 | 100 | 0 | 20 | 90 | 0 |
| 21. | 0 | 0 | 0 | 80 | 50 | 0 | 20 | 77 | 0 |
| 22. | 0 | 0 | 0 | 30 | 50 | 0 | 53 | 40 | 0 |
| 23. | 67 | 33 | 0 | 80 | 80 | 0 | 40 | 100 | 0 |
| 24. | 27 | 28 | 0 | 10 | 20 | 0 | 0 | 0 | 0 |
| 25. | 0 | 0 | 0 | 50 | 50 | 0 | 47 | 47 | 0 |
| 26. | 10 | 17 | 0 | 5 | 10 | 0 | 0 | 0 | 0 |
| 27. | 33 | 33 | 0 | 50 | 70 | 0 | 30 | 45 | 0 |
| 28. | 0 | 33 | 0 | 80 | 60 | 0 | 67 | 93 | 0 |
| 29. | 0 | 0 | 0 | 30 | 30 | 0 | 10 | 27 | 0 |
| 30. | 0 | 0 | 0 | 20 | 20 | 0 | 33 | 47 | 0 |
| 31. | 0 | 47 | 0 | 20 | 80 | 0 | 40 | 93 | 0 |
| 32. | 0 | 0 | 0 | 10 | 30 | 0 | 40 | 93 | 0 |
| 33. | 0 | 0 | 0 | 20 | 40 | 0 | 37 | 67 | 0 |
| 34. | 0 | 0 | 0 | 50 | 50 | 10 | 40 | 73 | 0 |
| 35. | 0 | 0 | 0 | 30 | 50 | 20 | 13 | 40 | 10 |
| 36. | 0 | 33 | 0 | 80 | 80 | 0 | 77 | 100 | 0 |
| 37. | 0 | 22 | 0 | 50 | 90 | 0 | 77 | 67 | 0 |
| 38. | 0 | 0 | 0 | 30 | 50 | 0 | 67 | 93 | 0 |
| 39. | 0 | 0 | 0 | 20 | 80 | 0 | 20 | 70 | 0 |
| 40. | 0 | 0 | 0 | 20 | 50 | 0 | 13 | 47 | 0 |
| 41. | 13 | 80 | 0 | 20 | 80 | 0 | 20 | 70 | 0 |
| 42. | 0 | 0 | 0 | 30 | 90 | 0 | 27 | 97 | 0 |
| 43. | 0 | 0 | 0 | 20 | 90 | 0 | 10 | 93 | 0 |
| 44. | 0 | 0 | 0 | 50 | 90 | 0 | 40 | 77 | 0 |
| 45. | 0 | 100 | 0 | 90 | 80 | 0 | 50 | 83 | 0 |
| 46. | 0 | 0 | 0 | 50 | 80 | 0 | 20 | 87 | 0 |
| 47. | 0 | 0 | 0 | 20 | 80 | 0 | 23 | 80 | 0 |
| 48. | 0 | 0 | 0 | 20 | 90 | 0 | 17 | 97 | 0 |
| 49. | 0 | 60 | 0 | 50 | 100 | 0 | 30 | 100 | 0 |
| 50. | 0 | 0 | 0 | 50 | 100 | 0 | 13 | 100 | 0 |
| 51. | 0 | 0 | 0 | 20 | 80 | 0 | 13 | 87 | 0 |
| 52. | 0 | 0 | 0 | 20 | 90 | 0 | 13 | 93 | 0 |
| 53. | 0 | 0 | 0 | 90 | 100 | 0 | 83 | 100 | 0 |
| 54. | 0 | 0 | 0 | 90 | 100 | 0 | 67 | 100 | 0 |
| 55. | 0 | 33 | 0 | 60 | 100 | 0 | 67 | 100 | 0 |
| 56. | 0 | 0 | 0 | 80 | 100 | 0 | 67 | 73 | 0 |
| 57. | 0 | 0 | 0 | 10 | 50 | 0 | 0 | 67 | 0 |
| 58. | 0 | 0 | 0 | 90 | 100 | 0 | 67 | 100 | 0 |
| 59. | 0 | 0 | 0 | 30 | 80 | 0 | 50 | 83 | 0 |
| 60. | 3 | 67 | 0 | 30 | 80 | 0 | 30 | 87 | 0 |
| 61. | 0 | 0 | 0 | 80 | 80 | 0 | 67 | 73 | 0 |
| 62. | 0 | 0 | 0 | 20 | 30 | 0 | 20 | 73 | 0 |
| 63. | 0 | 37 | 0 | 30 | 100 | 0 | 20 | 73 | 0 |
| 64. | 50 | 33 | 0 | 40 | 100 | 0 | 67 | 100 | 0 |
| 65. | 67 | 33 | 0 | 90 | 90 | 0 | 70 | 97 | 0 |
| 66. | 67 | 43 | 0 | 90 | 100 | 0 | 70 | 100 | 0 |
| 67. | 0 | 0 | 0 | 10 | 50 | 0 | 10 | 83 | 0 |
| 68. | 67 | 33 | 0 | 30 | 100 | 0 | 33 | 100 | 0 |
| 69. | 0 | 0 | 0 | 80 | 90 | 0 | 57 | 100 | 0 |
| 70. | 33 | 67 | 0 | 20 | 100 | 0 | 10 | 100 | 0 |
| 71. | 33 | 0 | 0 | 80 | 100 | 0 | 63 | 100 | 0 |
| 72. | 0 | 0 | 0 | 30 | 30 | 0 | 40 | 50 | 0 |
| 73. | 0 | 0 | 0 | 20 | 90 | 0 | 10 | 100 | 0 |

TABLE II-continued

| | % Control, 4 kg/ha | | | | | | | | |
|---|---|---|---|---|---|---|---|---|---|
| | Pre-emergence | | | Post-emergence | | | | | |
| | 18 DAT | | | 6 DAT | | | 18 DAT | | |
| Compound No. | GR avg. | Bl avg. | NS | GR avg. | BL avg. | NS | GR avg. | BL avg. | NS |
| 74. | 0 | 0 | 0 | 90 | 100 | 0 | 93 | 100 | 0 |
| 75. | 0 | 0 | 0 | 80 | 30 | 0 | 73 | 30 | 0 |
| 76. | 0 | 0 | 0 | 30 | 50 | 0 | 27 | 40 | 0 |
| 77. | 0 | 0 | 0 | 80 | 80 | 0 | 93 | 83 | 0 |
| 78. | 0 | 0 | 0 | 90 | 90 | 0 | 93 | 93 | 0 |
| 79. | 33 | 67 | 0 | 80 | 100 | 0 | 87 | 100 | 0 |
| 80. | 33 | 0 | 0 | 50 | 100 | 0 | 60 | 100 | 0 |
| 81. | 33 | 67 | 0 | 60 | 100 | 0 | 57 | 100 | 0 |
| 82. | 0 | 0 | 0 | 50 | 100 | 0 | 40 | 100 | 0 |
| 83. | 0 | 0 | 0 | — | — | — | 70 | 100 | 0 |
| 84. | 0 | 7 | 0 | 50 | 90 | 0 | 73 | 100 | 5 |
| 85. | 0 | 0 | 0 | 20 | 80 | 0 | 40 | 93 | 0 |
| 86. | 0 | 0 | 0 | 50 | 90 | 0 | 23 | 86 | 0 |
| 87. | 23 | 10 | 0 | 20 | 85 | 10 | 3 | 60 | 5 |
| 88. | 0 | 0 | 0 | 30 | 85 | 20 | 10 | 83 | 5 |
| 89. | 3 | 0 | 0 | 25 | 70 | 10 | 3 | 68 | 5 |
| 90. | 0 | 0 | 0 | 30 | 75 | 10 | 33 | 90 | 5 |
| 91. | 25 | 0 | 0 | 40 | 85 | 10 | 10 | 83 | 5 |
| 92. | 16 | 0 | 0 | 30 | 75 | 10 | 16 | 83 | 5 |
| 93. | 0 | 13 | 0 | 50 | 90 | 10 | 16 | 95 | 5 |
| 94. | 10 | 50 | 0 | 30 | 80 | 10 | 10 | 75 | 5 |
| 95. | 3 | 0 | 0 | 40 | 90 | 5 | 6 | 96 | 0 |
| 96. | 3 | 0 | 0 | 50 | 90 | 20 | 16 | 91 | 30 |
| 97. | 23 | 0 | 0 | 30 | 95 | 10 | 13 | 96 | 5 |
| 98. | 0 | 0 | 0 | 30 | 85 | 5 | 15 | 78 | 0 |
| 99. | 0 | 0 | 0 | 50 | 100 | 0 | 50 | 100 | 0 |

Selected compounds were further tested against the same weeds at a lower application rate of 1.5 kg/ha. In general, control of grassy weeds was lower, but for the most part, control of broadleaf weeds remained at 80% or above.

In practice, a pure compound can be used as a herbicide. However, in general, the compounds are first formulated with one or more inert carriers or diluents suitable for herbicidal use, before being applied.

The compositions or formulations, including a compound as described herein, may exist in any one of a number of solid or liquid forms. Examples of liquid forms are emulsifiable concentrates, flowables and pastes. Such compositions may contain, in addition to the active compound or compounds, various carriers or diluents; surface active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcium carbonate, silica, kieselguhr, clay, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles. Pellets or granules can be manufactured by extrusion with appropriate carriers and binders.

Wettable powders, flowables, and pastes are obtained by mixing and grinding an active compound with one or more dispersing agents and/or solid carriers or diluents. Also included, may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents are generally also added.

The compositions may also be used in the form of microcapsules. Microcapsules consist of fully enclosed or encapsulated droplets or granules containing the active compound, enclosed within an inert porous membrane, so as to permit escape of the encapsulated material into the surrounding medium or environment at a controlled rate.

Useful encapsulating materials include natural and synthetic rubbers or latexes, cellulosic materials, styrenebutadiene copolymers, polyacrylonitriles, polyacrylates, polyesters, polyamides, polyurethanes and starch xanthates.

It is possible to use highly concentrated liquid compositions containing up to about 95% by weight of the active compound, or even the active compound alone for those compounds which are liquids, when applying the compound in the form of a finely divided liquid by use of various atomizing equipment, for example by airplane crop-spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: Wettable powders, flowables and pastes—20 to 90% active compound; oil suspensions, emulsions, solutions and emulsifiable concentrates—5 to 90% active compound; aqueous suspensions —10 to 50% active compound; dusts and powders—1 to 25% active compound; granules and pellets —1 to 20% active compound.

The rate of application of the active compound to a locus to be controlled will depend on the activity of the compound and/or composition and the nature of the seeds and plants to be controlled and will vary from about 0.05 to about 50 pounds per acre (about 0.06 to about 56 kg/ha).

Compositions containing one or more of the active compounds described, in a herbicidally effective amount, may be applied to the plant or locus to be controlled in any conventional manner. Thus, powders and various liquid compositions containing the active compound can be applied by the use of power dusters, boom and hand sprayers and spray spray dusters, or applied from airplanes as mists or sprays. When applied in the latter method, they may be effective in very low dosages. To modify or control growth of germinating seeds or emerging seedlings, liquid compositions may be applied to the soil with conventional methods and may be distributed in the soil to a depth of one-half inch below the soil surface. The compositions need not be admixed with the soil particles, but can be applied merely by sprinkling on the surface of the soil.

Compositions including active compounds may also be applied by addition to irrigation waters supplied to the field to be treated. This method of application permits penetration of the compounds into the soil as the water is absorbed therein.

EXAMPLES OF TYPICAL COMPOSITIONS

| Ingredient | Weight % | | |
|---|---|---|---|
| Oil | | | |
| Active Compound | 1 | | |
| Oil solvent-heavy aromatic naphtha | 99 | | |
| Total | 100 | | |
| Emulsifiable Concentrate | | | |
| Active Compound | 50 | | |
| Kerosene | 45 | | |
| Emulsifying agent (mixture of long chain ethoxylated polyethers with long chain sulfonate) | 5 | | |
| Total | 100 | | |
| Emulsifiable Concentrate | | | |
| Active Compound | 90 | | |
| Kerosene | 5 | | |
| Emulsifying agent (mixture of long chain ethoxylated polyethers with long chain sulfonate) | 5 | | |
| Total | 100 | | |
| Dusts and/or Powders | | | |
| Ingredient | Wt. % | Wt. % | Wt. % |
| Active Compound | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| TOTAL | 100.0 | 100.0 | 100.0 |

The compositions of the invention may comprise, in addition to one or more compounds of the invention, one or more compounds not of the invention but which possess biological activity. Compounds not of this invention maybe other pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus. Accordingly, in yet a still further embodiment, the invention provides an herbicidal composition comprising a mixture of at least one herbicidal compound of formula (I) as hereinbefore defined with at least one other herbicide.

The other herbicide may be any herbicide not having the formula (I). It will generally be an herbicide having a complementary action in the particular application.

Examples of useful complementary herbicides include:

A. Benzo-2,1,3-thiodiazin-4-one-2,2-dioxides such as 3-isopropylbenzo-2,1,3-thiadiazin-4-one-2,2-dioxide (bentazone);

B. hormone herbicides, particularly the phenoxy alkanoic acids such as 4-chloro-2-methylphenoxyacetic acid (MCPA), S-ethyl 4-chloro-O-tolyloxy thioacetate (MCPA-thioethyl), 2-(2,4-dichlorophenoxy) propionic acid (dichlorprop), 2,4,5-trichlorophenoxyacetic acid (2,4,5-T), 4-(4-chloro-2-methylphenoxy)butyric acid (MCPB), 2,4-dichlorophenoxyacetic acid (2,4-D), 4-(2,4-dichlorophenoxy)butyric acid (2,4-DB), 2-(4-chloro-2-methylphenoxy) propionic acid (mecoprop), 3,5,6-trichloro-2-pyridyloxyacetic acid (trichlopyr), 4-amino-3,5-dichloro-6-fluoro-2-pyridyloxyacetic acid (fluroxypyr), 3,6-dichloropyridine-2-carboxylic acid (clopyralid), and their derivatives (e.g. salts, esters and amides);

C. 1,3-dimethylpyrazole derivatives such as 2-[4-(2,4-dichlorobenzoyl) 1,3-dimethylpyrazol-5-yloxy]acetophenone (pyrazoxyfen), 4-(2,4-dichlorobenzoyl)1,3-dimethylpyrazol-5-yltoluene sulfonate (pyrazolate) and 2-[4-(2,4-di-chloro-m-toluolyl)-1,3-dimethylpyrazol-5-yloxy]-4'-methylacetophenone (benzofenap);

D. Dinitrophenols and their derivatives (e.q. acetates such as 2-methyl-4,6-dinitrophenol (DNOC), 2-t-butyl-4,6-dinitrophenol (dinoterb), 2-sec.-butyl-4,6-dinitrophenol (dinoseb) and its ester, dinoseb acetate;

E. dinitroaniline herbicides such as N',N'-diethyl-2,6-dinitro-4-trifluoromethyl-m-phenylenediamine (dinitramine), 2,6-dinitro-N,N-dipropyl-4-trifluoromethylaniline (trifluralin), N-ethyl-N-(2-methylallyl)-2,6-dinitro4-trifluoromethylaniline (ethalfluralin), N-(1-ethylpropyl)-2,6-dinitro-3,4-xylidine (pendimethalin); and 3,5-dinitro-$N^4$, $N^4$-dipropyl-sulphanilamide (oryzalin);

F. arylurea herbicides such as N'-(3,4-dichlorophenyl)-N,N-dimethylurea (diuron), N,N-dimethyl-N'-[3-(trifluoromethyl) phenyl]urea (flumeturon), 3-(3-chloro-4-methoxyphenyl)-1,1-dimethylurea (metoxuron), 1-butyl-3-(3,4-dichlorophenyl)-1-methylurea (neburon), 3-(4-isopropylphenyl)-1,1-dimethylurea (isoproturon), 3-(3-chloro-p-tolyl)-1,1-dimethylurea (chlorotoluron), 3-[4-(4-chlorophenoxy) phenyl]-1,1-dimethylurea (chloroxuron), 3-(3,4-dichlorophenyl)-1-methylurea (linuron), 3-(4-chlorophenyl)-1-methoxy-1-methylurea (monolinuron), 3-(4-bromo-4-chlorophenyl)-1-methoxy-1methylurea (chlorobromuron), 1-(1-methyl-1-phenylethyl)-3-ptolylurea (daimuron), and 1-benzothiazol-2-yl-1,3-dimethylurea (methabenzthiazuron);

G. phenylcarbamoyloxyphenylcarbamates such as 3-[methoxycarbonylamino]phenyl (3-methylphenyl)- carbamate (phenmedipham) and 3-[ethoxycarbonylamino]-phenyl phenylcarbamate (desmedipham);

H. 2-phenylpyridazin-3-ones such as 5-amino-4-chloro-2-phenylpyridazin-3-one (chloridazon), and 4-chloro-5-methylamino-2-(α,α,α-trifluoro-m-tolyl) pyridazin-3(2H)-one (norflurazon);

I. uracil herbicides such as 3-cyclohexyl-5,6-trimethyleneuracil (lenacil), 5-bromo-3-sec.-butyl-6-methyluracil (bromacil) and 3-t-butyl-5-chloro-6-methyl-uracil (terbacil);

J. triazine herbicides such as 2-chloro-4-ethyl-amino-6-(i-propylamino)-1,3,5-triazine (atrazine), 2-chloro-4,6-di(ethylamino)-1,3,5-triazine (simazine), 2-azido-4-(i-propylamino)-6-methylthio-1,3,5-triazine (aziprotryne), 2-(4-chloro-6-ethylamino-1,3,5-triazin-2-ylamino)-2-methylpropionitrile (cyanazine), $N^2$, $N^4$-di-isopropyl-6-methylthio-1,3,5-triazine- 2,4-diamine (prometryn), $N^2$-(1,2-dimethylpropyl)$N^4$-ethyl-6-methylthio-1,3,5-triazine-2,4-diamine (dimethametryn), $N^2$,$N^4$-diethyl-6-methylthio-1,3,5-triazine-2,4-diamine (simetyrne), and $N^2$-tert.-butyl-$N^4$-ethyl-6-methylthio-1,3,5-triazinetryne), 2,4-diamine (terbutryn);

K. phosphorothioate herbicides such as S-2-methylpiperidinocarbonyl-methyl O,O-dipropyl phosphorodithioate (piperophos), S-2-benzenesulphonamidoethyl O,O-diisopropyl phosphonodithioate (bensulide), and O-ethyl O-6-nitro-m-tolyl sec.-butylphosphoramidothioate (butamifos);

L. thiolcarbamate herbicides such as S-ethyl N-cyclohexyl-N-ethyl thiocarbamate (cycloate), S-propyl di-propyl-thiocarbamate (vernolate), S-ethyl-azepine-1-carbothioate (molinate), S-4-chlorobenzyl diethylthiocarbamate (thiobencarb), S-ethyl di-isobutyl-thiocarbamate (butylate)*, S-ethyl di-isopropylthiocarbamate (EPTC)*, S-2,3,3-trichloroallyl di-isopropyl thiocarbamate (triallate), S-2,3-dichloroallyl di-isopropyl thiocarbamate (diallate), S-benzyl 1,2-dimethylpropyl (ethyl) thiocarbamate (esprocarb), S-benzyl di(sec.-butyl) thiocarbamate (tiocarbazil), 6-chloro-3-phenylpyridazin-4-yl S-octyl thiocarbamate (pyridate), and S-1-methyl-1-phenylethyl-piperidine-1-carbothioate (dimepiperate);

*These compounds are preferably employed in combination with a safener such as 2,2-dichloro-N,N-di-2-propenylacetamide (dichlormid).

M. 1,2,4-triazin-5-one herbicides such as 4-amino-4,5-dihydro-3-methyl-6-phenyl-1,2,4-triazine-5-one (metamitron) and 4-amino-6-butyl-4,5-dihydro-3-methylthio-1,3,4-triazin-5-one (metribuzin);

N. benzoic acid herbicides such as 2,3,6-trichlorobenzoic acid (2,3,6-TBA), 3,6-dichloro-2-methoxybenzoic acid (dicamba) and 3-amino-2,5-dichlorobenzoic acid (chloramben);

O. anilide herbicides such as 2-chloro-2,,6,-diethyl-N-(2-propoxyethyl)acetanilide (pretilachlor), N-butoxymethyl-2-chloro-2',6'-diethylacetanilide (butachlor), the corresponding N-methoxy compound (alachlor), the corresponding N-i-propyl compound (propachlor), 3',4'-dichloropropionanilide (propanil), 2-chloro-N-[pyrazol-1-ylmethyl]acet-2'-6'xylidide-(metazachlor), 2-chloro-6'-ethyl-N-(2-methoxy-1-methylethyl) acetotoluidide (metolachlor), 2-chloro-N-ethoxymethyl-6'-ethylacetotoluidide (acetochlor), and 2-chloro-N-(2-methoxyethyl)acet-2',6'-xylidide (dimethachlor);

P. dihalobenzonitrile herbicides such as 2,6-dichlorobenzonitrile (dichlobenil), 3,5-dibromo-4-hydroxy-benzonitrile (bromoxynil) and 3,5-diiodo-4-hydroxy-benzonitrile (ioxynil);

Q. haloalkanoic herbicides such as 2,2-dichloropropionic acid (dalapon), trichloroacetic acid (TCA) and salts thereof;

R. diphenylether herbicides such as ethyl 2-[5-(2-chloro-trifluoro-p-tolyloxy)-2-nitrobenzoyl]oxy propionate (lactofen), D-[5-(2-chloro-α,α,α-trifuoro-p-tolyl)-2-nitrobenzoyl]glycolic acid (fluroglycofen) or salts or esters thereof, 2,4-dichlorophenyl-4-nitrophenyl ether (nitrofen), methyl-(2,4-dichlorophenoxy)-2-nitrobenzoate (bifenox), 2-nitro-5-(2-chloro-4-trifluoromethylphenoxy) benzoic acid (acifluorfen) and salts and esters thereof, 2-chloro-4-trifluoromethylphenyl 3-ethoxy-4-nitrophenyl ether (oxyfluorfen) and 5-[2-chloro-4-(trifluoromethyl)phenoxy]-N-(methylsulfonyl)-2-nitrobenzamide (fomesafen); 2,4,6-trichlorophenyl 4-nitrophenyl ether (chlornitrofen) and 5-(2,4-dichlorophenoxy)-2-nitroanisole (chlomethoxyfen);

S. phenoxyphenoxypropionate herbicides such as (RS)-2-[4-(2,4-dichlorophenoxy) phenoxy]propionic acid (diclofop) and esters thereof such as the methyl ester, 2-[4-(5-trifluoromethyl)-2-(pyridinyl)oxy]phenoxypropanoic acid (fluazifop) and esters thereof, 2-[4-(3-chloro-5-trifluoromethyl)-2-pyridinyl)oxy]phenoxypropanoic acid (haloxyfop) and esters thereof, 2-[4-(6-chloro-2-quinoxalinyl)oxy]phenoxypropanoic acid (quizalofop) and esters thereof and (±)-2-[4-(6-chlorobenzoxazol-2-yloxy)phenoxy]propionic acid (fenoxaprop) and esters thereof such as the ethyl ester;

T. cyclohexanedione herbicides such as 2,2-dimethyl-4,6-dioxo-5-[1-(2-propenyloxyimino)butyl]cyclohexane carboxylic acid (alloxydim) and salts thereof, 2-(1-ethoxyimino) butyl-5-[2-(ethylthio)-propyl]-3-hydroxy-2-cyclohexan1-one (sethoxydim), 2-(1-ethoxyimino)butyl-3-hydroxy-5-thian3-ylcyclohex-2-enone (cycloxydim), 2-[1(ethoxyimino)propyl]-3-hydroxy-5-mesityl-cyclohex-2-enone (tralkoxydim), and (±)-2-(E)- 1-[(E)-3-chloroallyloximino]propyl-5-[2-(ethylthio)propyl]-3-hydroxycyclohex-2-enone (clethodim);

U. sulfonyl urea herbicides such as 2-chloro-N (4-methoxy-6-methyl-1,3,5-triazin-2-yl)-aminocarbonyl) benzenesulphonamide (chlorosulfuron), methyl 2-[([(4,6-dimethyl-2-pyrimidinyl)amino]-carbonyl)amino]-sulphonylbenzoic acid (sulfometuron), 2-([(3-(4-methoxy-6-methyl-1,3,5-triazin-2-yl)carbonyl]amino)-sulphonyl)benzoic acid (metsulfuron) and esters thereof; -(4,6-dimethoxypyrimidin-2-ylcarbamoylsuphamoyl)-O-toluic acid (benzsulfuron) and esters thereof such as the ester thereof methyl, 3-[3-(4-methoxy-6-methyl-1,3,5-triazin-2-yl)ureido- sulphonyl]-thiophene-2-carboxylate (DPX-M6313), 2-(4-chloro-6-methoxy pyrimidin-2-yl carbamoylsulphamoyl benzoic acid (chlorimuron) and esters such as the ethyl ester thereof, 2-(4,6-dimethoxypyrimidin-2-ylcarbamoylsulphamoyl)-N,N-dimethyl-nicotinamide, 2-[4,6-bis(difluoromethoxy)pyrimidin-2-ylcarbamoylsulphamoyl]-benzoic acid (pirimisulfuron) and esters such as the methyl ester thereof, 2-[3-(4-methoxy-6-methyl-1,3,5-triazin-zyl)-3-methylureidosulphonyl]benzoic acid esters such as the methyl ester thereof (DPX-LS300) and 5-(4,6-dimethoxypyrimidin-2-ylcarbamoylsulphamoyl)-1-methylpyrazole-4-carboxylic acid (pyrazosulfuron);

V. imidazolidinone herbicides such as 2-(4,5-dihydro-4-isopropyl-4-methyl-5-oxoimidazol-2-yl) quinoline-3-carboxylic acid (imazaquin), methyl 6-(4-isopropyl-4-methyl-5-oxo-2-imidazolin-2-yl)-m-toluate and p-toluate isomer (imazamethabenz), 2-(4-isopropyl-4-methyl-5-oxo-2-imidazolin-2-yl) nicotinic acid (imazapyr) and isopropylammonium salts thereof, (RS)-5-ethyl-2-(4-isopropyl-4-methyl-5-oxo-2-imidazolin-2-yl) nicotinic acid (imazethapyr);

W. arylanilide herbicides such as benzoyl-N-(3-chloro-4-fluorophenyl)-L-alanine (flamprop) and esters thereof, ethyl N-benzoyl-N-(3,4-dichlorophenyl)-DL-alaninate (benzoylprop-ethyl), N-(2,4-difluorophenyl)-2-(3-trifluoromethyl)phenoxy3-pyridinecarboxamide (diflufenican);

X. amino acid herbicides such as N-(phosphonomethyl)-glycine (glyphosate) and DL-homoalanin-4-yl (methyl)-phosphinic acid (gluyfosinate) and their salts and esters, trimethylsulfonium N-(phosphonomethyl)-glycine (sulphosate), and bilanafos;

Y. organoarsenical herbicides such as monosodium methanearsonate (MSMA);

Z. herbicidal amide derivative such as (RS)-N,N-diethyl-2-(1-naphthyloxypropionamide) (napropamide), 3,5-dichloro-N-(1,1-dimethylpropynyl)benzamide (propyzamide), (R)-1-(ethylcarbamoyl)ethyl carbanilate (carbetamide), N-benzyl-N-isopropylpivalamide (tebutam), (RS)-2-bromo-N-($\alpha,\alpha$-dimethylbenzyl)-3,3-dimethylbutyramide (bromobutide), N-[3-(1-ethyl-1-methylpropyl)-isoxazol-5-yl]2,6-dimethoxybenzamide, (isoxaben), N-phenyl-2-(2-naphthyloxy) propionamide (naproanilide), N,N-dimethyl-diphenylacetamide (diphenamid), and N-(1-naphthyl)phthalamic acid (naptalam);

AA. miscellaneous herbicides including 2-ethoxy-2,3-dihydro-3,3-dimethylbenzofuran methanesulfonate (ethofumesate), 7-oxabicyclo (2.2.1)heptane,1-methyl-4-(1-methylethyl)-2-(2-methylphenylmethoxy)-exo (cinmethylin), 1,2-dimethyl-3,5-diphenylpyrazolium ion (difenzoquat) and salts thereof such as the methyl sulfate salt, 2-(2-chlorobenzyl)-4,4-dimethyl-1,2-isopropoxyphenyl)-1,3,4-oxadiazol-2(3H)-one (oxadiazon), 3,5-dibromo-4-hydroxy benzaldehyde 2,4-dinitrophenyloxime (bromofenoxim), 4-chlorobut-2-ynyl-3-chlorocarbanilate (barban), (RS)-2-(3,5-dichlorophenyl)-2-(2,2,2-trichloroethyl)oxirane (tridiphane), (3RS,4RS;3RS,4SR)-3-chloro-4-chloromethyl-1-$\alpha,\alpha$,-$\alpha$-trifluro-m-tolyl-2-pyrrolidone (in the ratio 3:1) (fluorochloridone), dichloroquinoline 8-carboxylic acid (quinchlorac) and 2-(1,3-benzothiazol-2-yl-oxy)-N-methylacetanilide (mefanacet);

BB. examples of useful contact herbicides include bipyridylium herbicides such as those in which the active entity is the 1,1'-dimethyl-4,4'-dipyridylium ion (paraquat) and those in which the active entity is the 1,1'-ethylene-2,2'-dipyridylium ion (diquat).

What is claimed is:

1. A compound having the formula

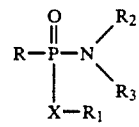

in which

R is $C_3$-$C_6$ alkyl or $C_3$-$C_6$ cycloalkyl;

X is oxygen or sulfur;

$R_1$ is $C_2$-$C_{12}$ alkyl, $C_3$-$C_6$ cycloalkyl optionally substituted with up to 2 $C_1$-$C_3$ allyl groups, phenyl, or substituted phenyl having from 1 to 2 substituents selected from halo, nitro, $C_1$-$C_4$ alkyl, $C_1$-$C_4$ alkoxy, $C_1$-$C_4$ thioalkyl, $C_3$-$C_4$ alkenyl, $C_1$-$C_1$-$C_4$ alkoxycarbonyl, and phenyl;

$R_2$ is $C_1$-$C_6$ alkyl or $C_3$-$C_6$ cycloalkyl; and $R_3$ is phenyl or substituted phenyl having from 1 to 2 substituents selected from $C_1$-$C_4$ alkyl, $C_1$-$C_4$ alkoxy, $C_1$-$C_4$ haloalkyl and halogen;

provided that: if R is n-propyl and X is oxygen, then neither $R_1$ nor $R_2$ is ethyl.

2. A compound according to claim 1 in which R is $C_3$-$C_6$ alkyl or $C_5$-$C_6$ cycloalkyl.

3. A compound according to claim 1 in which $R_1$ is $C_2$-$C_{12}$ alkyl, $C_3$-$C_6$ cycloalkyl optionally substituted by up to two methyl groups or phenyl, optionally substituted by one $C_1$-$C_4$ alkyl group.

4. A compound according to claim 3 in which $R_2$ is $C_1$-$C_6$ alkyl or $C_3$-$C_6$ cycloalkyl.

5. A compound according to claim 1 in which $R_1$ is $C_3$-$C_4$ alkyl.

6. A compound according to claim 1 in which $R_1$ is a propyl group.

7. A compound according to claim 6 in which $R_1$ is ispropyl.

8. A compound according to claim 1 in which $R_1$ is a butyl group.

9. A compound according to claim 8 in which $R_1$ is sec.-butyl.

10. A compound according to claim 9 in which X is oxygen.

11. A compound according to claim 9 in which X is sulfur.

12. A compound according to claim 1 in which $R_2$ is $C_1$-$C_4$ alkyl and $R_3$ is phenyl or substituted phenyl.

13. A compound according to claim 12 in which $R_3$ is phenyl or substituted phenyl in which the substituents are selected from chloro, fluoro, nitro, methyl, ethyl, i-propyl, t-butyl, methoxy, ethoxy, trifluoromethyl, and combinations thereof.

14. An herbicidal composition comprising (a) an herbicidally effective amount of a compound according to claim 1 and (b) an inert diluent or carrier suitable for use with herbicides.

* * * * *